United States Patent
Nakamura

(10) Patent No.: US 11,274,211 B2
(45) Date of Patent: Mar. 15, 2022

(54) GLITTER PIGMENT HAVING ELECTROMAGNETIC WAVE TRANSMISSION PROPERTIES, COMPOSITION INCLUDING THE PIGMENT, AND PAINTED PRODUCT INCLUDING THE PIGMENT

(71) Applicant: Nippon Sheet Glass Company, Limited, Tokyo (JP)

(72) Inventor: Koichiro Nakamura, Kanagawa (JP)

(73) Assignee: NIPPON SHEET GLASS COMPANY, LIMITED, Tokyo (JP)

( * ) Notice: Subject to any disclaimer, the term of this patent is extended or adjusted under 35 U.S.C. 154(b) by 182 days.

(21) Appl. No.: 16/608,069

(22) PCT Filed: Apr. 27, 2017

(86) PCT No.: PCT/JP2017/016853
§ 371 (c)(1),
(2) Date: Oct. 24, 2019

(87) PCT Pub. No.: WO2018/198294
PCT Pub. Date: Nov. 1, 2018

(65) Prior Publication Data
US 2020/0190330 A1    Jun. 18, 2020

(51) Int. Cl.
*C09C 1/00* (2006.01)
*C09D 7/40* (2018.01)

(52) U.S. Cl.
CPC .............. *C09C 1/0015* (2013.01); *C09D 7/70* (2018.01); *C01P 2004/20* (2013.01);
(Continued)

(58) Field of Classification Search
CPC .. A61K 8/0266; C01P 2004/20; C09C 1/0015; C09C 2200/301–302
See application file for complete search history.

(56) References Cited

U.S. PATENT DOCUMENTS 6,936,348 B1    8/2005  Yanagase
7,344,590 B2*   3/2008  Schmidt ................ C09C 1/0015
                                                106/31.64
(Continued)

FOREIGN PATENT DOCUMENTS

JP    2001031421    2/2001
JP    2004091507    3/2004
(Continued)

OTHER PUBLICATIONS

Office Action issued for Chinese Patent Application No. 201780090046. 9, dated Nov. 11, 2020, 11 pages including English machine translation.

(Continued)

*Primary Examiner* — Alexandre F Ferre
(74) *Attorney, Agent, or Firm* — Hamre, Schumann, Mueller & Larson, P.C.

(57) ABSTRACT

The present invention provides a glitter pigment capable of simultaneously achieving electromagnetic wave transmission properties, a high reflectance in appearance, and a neutral color in appearance. The glitter pigment according to the present invention includes: a glass flake 1; and a titanium oxide layer 2 and a silver layer 3 formed in this order on the glass flake 1, wherein a product of the optical thickness of the glass flake 1 and the optical thickness of the titanium oxide layer 2 is 61000 or more and 66000 or less when the optical thickness is expressed in nm, and the silver layer 3 has a physical thickness of 35 nm or more and 55 nm or less.

8 Claims, 2 Drawing Sheets

(52) U.S. Cl.
CPC .... *C09C 2200/102* (2013.01); *C09C 2200/24* (2013.01); *C09C 2200/301* (2013.01); *C09C 2200/302* (2013.01); *C09C 2210/00* (2013.01)

(56) References Cited

U.S. PATENT DOCUMENTS

| | | | |
|---|---|---|---|
| 2004/0112253 A1* | 6/2004 | Zimmermann | ....... C09C 1/0015 106/415 |
| 2010/0116169 A1 | 5/2010 | Kaupp et al. | |
| 2013/0164356 A1 | 6/2013 | Pfaff et al. | |
| 2018/0133116 A1 | 5/2018 | Hioki | |

FOREIGN PATENT DOCUMENTS

| | | |
|---|---|---|
| JP | 2006299051 | 11/2006 |
| JP | 2008546880 | 12/2008 |
| JP | 2009091411 | 4/2009 |
| JP | 2009102626 | 5/2009 |
| JP | 2009242795 | 10/2009 |
| JP | 2010030075 | 2/2010 |
| JP | 2010538096 | 12/2010 |
| JP | 2012025823 | 2/2012 |
| JP | 2013129831 | 7/2013 |
| WO | 2007054379 | 5/2007 |
| WO | 2010125885 | 11/2010 |
| WO | 2016194902 | 12/2016 |

OTHER PUBLICATIONS

Zhu, Jia-qi et al., "Infrared Antireflection Protective Film Material," National Defense Industry Press, 2015, pp. 124-127. (See English translation of Chinese Office Action for relevance.).

Wang, X. et al., "Production and Application of Nanometer Titanium Dioxide," Guizhou Science and Technology Publishing House, 2014, pp. 19-24. (See English translation of Chinese Office Action for relevance.).

International Search Report and Written Opinion issued for International Patent Application No. PCT/JP2017/016853, dated Jul. 18, 2017, 8 pages including English translation of Search Report.

* cited by examiner

GLITTER PIGMENT HAVING ELECTROMAGNETIC WAVE TRANSMISSION PROPERTIES, COMPOSITION INCLUDING THE PIGMENT, AND PAINTED PRODUCT INCLUDING THE PIGMENT

TECHNICAL FIELD

The present invention relates to glitter pigments, particularly relates to a glitter pigment including a glass flake as a substrate and a laminate film formed thereon, and more particularly relates to a glitter pigment having electromagnetic wave transmission properties and suitable for providing a high-brightness reflected light of a neutral color. The present invention also relates to a composition containing a glitter pigment and to a painted product having a paint film containing a glitter pigment.

BACKGROUND ART

Glitter pigments are added to various products to allow the products to reflect light with sparkles. One example of such products is a paint used to paint vehicles including automobiles. Flaky aluminum (aluminum flake) is often used as a glitter pigment included in paint films of vehicles. In terms of its small thickness and high reflectance, an aluminum flake is suitable for painting vehicles.

Along with development and dissemination of intelligent transport systems (ITS), the number of vehicles equipped with a sending-receiving device such as a millimeter-wave radar which sends and receives electromagnetic waves is increasing. This trend is expected to be accelerated further by progress in development of self-driving technology. Sending-receiving devices are commonly mounted on the inner side of a bumper or another non-metal component so that sending and receiving of electromagnetic waves will not be interfered. A paint in which an aluminum flake is used as a glitter pigment, however, prevents transmission of electromagnetic waves. For this reason, a paint that does not impair electromagnetic wave transmission properties when applied onto the surface of a non-metal component is demanded.

Patent Literature 1 proposes to ensure electromagnetic wave transmission properties by increasing distances between aluminum flakes in a paint film of vehicles. However, this proposal is essentially based on making a partial sacrifice of a high reflectance which the resultant glitter pigment could have.

It has also been proposed to use, instead of an aluminum flake, a glitter pigment including a thin metal film formed on the surface of a flaky inorganic substrate. The flaky inorganic substrate is specifically a glass flake, mica, or the like. For example, Patent Literature 2 discloses a glitter pigment including a silver alloy film formed on the surface of a flaky inorganic substrate. The silver alloy film includes, in addition to silver, at least one noble metal selected from gold, palladium, and platinum. This technique has been developed to overcome a disadvantage of a yellowish color resulting from covering a substrate with silver only. However, this glitter pigment has room for improvement in that not only silver but also a noble metal that is more expensive than silver is necessary, and is also unsuitable for providing a neutral color from which an unnecessary color is sufficiently removed.

CITATION LIST

Patent Literature

Patent Literature 1: JP 2010-030075 A
Patent Literature 2: JP 2009-102626 A

SUMMARY OF INVENTION

Technical Problem

In view of the above circumstances, the present invention aims to provide a glitter pigment having electromagnetic wave transmission properties and having a high reflectance and neutral color in appearance.

Solution to Problem

The present invention provides a glitter pigment including:
a glass flake; and
a titanium oxide layer and a silver layer formed in this order on the glass flake, wherein
a product of the optical thickness of the glass flake and the optical thickness of the titanium oxide layer is 61000 or more and 66000 or less when the optical thickness is expressed in nm, and
the silver layer has a physical thickness of 35 nm or more and 55 nm or less.

Advantageous Effects of Invention

The present invention provides a glitter pigment having electromagnetic wave transmission properties and having a high reflectance and neutral color in appearance.

DESCRIPTION OF EMBODIMENTS

Hereinafter, the present invention will be described in detail. The following description is not intended to limit the present invention to specific embodiments.

The term "neutral" as used herein refers to being a color whose absolute values of a* and b* are both 30 or less, preferably 28 or less, more preferably 25 or less, and particularly preferably 20 or less, in L*a*b* color system.

[Structure of Layers of Glitter Pigment]

Figure 1:
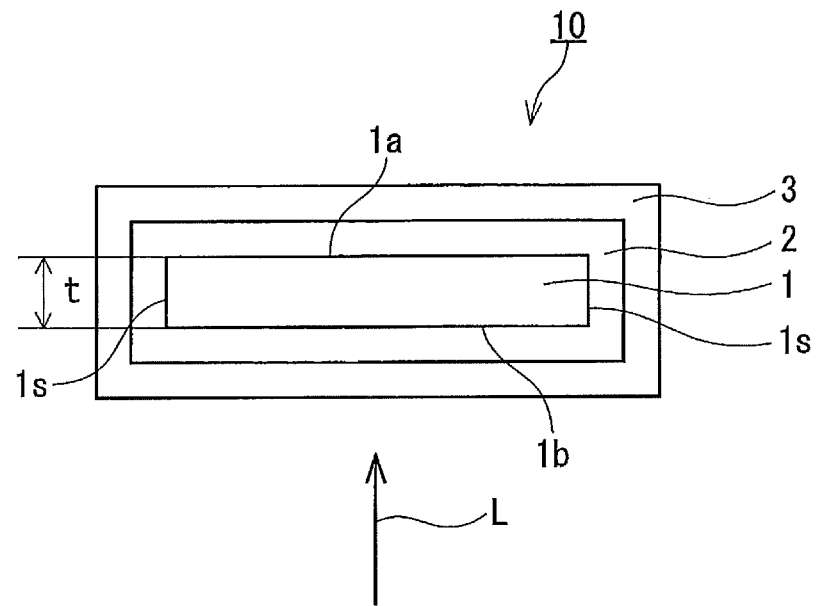
FIG. 1 is a cross-sectional view illustrating the structure of an embodiment of a glitter pigment according to the present invention.

In the embodiment shown in FIG. 1, a glitter pigment 10 includes: a glass flake 1; and a titanium oxide layer 2 and a silver layer 3 formed in this order on the glass flake 1. More specifically, the titanium oxide layer 2 and silver layer 3 are formed on both a first principal surface 1a and second principal surface 1b of the glass flake 1, the first principal surface 1a and second principal surface 1b being opposite to each other, and also formed on a side surface 1s. In other words, a laminate film composed of the titanium oxide layer 2 and silver layer 3 covers the entire glass flake 1. The first principal surface 1a and second principal surface 1b are a pair of surfaces substantially parallel to each other, and the distance therebetween corresponds to the thickness t of the glass flake 1.

Figure 2:
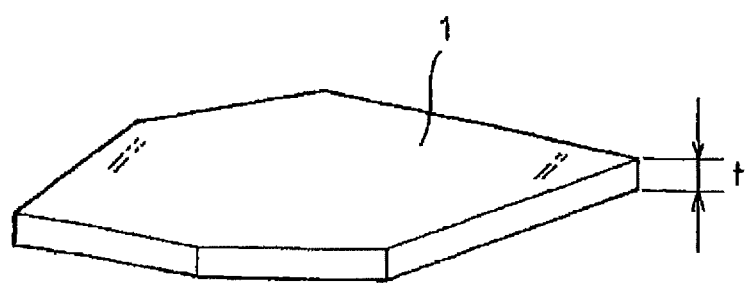
FIG. 2 is a perspective view illustrating an embodiment of a glass flake.

FIG. 2 shows a typical shape of the glass flake 1. As shown in FIG. 2, the glass flake 1 is, for example, a scale-like thin piece.

The glitter pigment 10 has the silver layer 3, titanium oxide layer 2, glass flake 1, titanium oxide layer 2, and silver layer 3 as an optical interference system along the direction of the thickness t of the glass flake 1. For conventionally common glitter pigments, the thickness of a coating alone, i.e., a coating portion exclusive of a substrate such as a glass flake, is adjusted. Unlike such glitter pigments, for the glitter pigment 10, the thickness of each layer of the five-layer optical interference system including the glass flake 1 which is a substrate is adjusted to control the optical properties.

Hereinafter, the glass flake 1, titanium oxide layer 2, and silver layer 3 will be described.

(Glass Flake)

The glass flake is a fine, plate-like glass substrate which can be called, for example, a scaly glass particle. The glass composition for forming the glass flake is not particularly limited. A glass composition containing silicon dioxide as a main component and further containing other metal oxides such as aluminum oxide, calcium oxide, and sodium oxide is typically used. The term "main component" is used herein to refer to a component whose content is highest in terms of mass. Examples of glass compositions that can be used include soda-lime glass, A-glass, C-glass, E-glass, borosilicate glass, and aluminosilicate glass. The refractive indices of these glass compositions, which have the same main component (silicon dioxide), are roughly in the range of 1.50 to 1.60, albeit differing slightly. As the glass composition, soda-lime glass, C-glass, E-glass, and borosilicate glass are preferred, and the refractive indices thereof are in the range of 1.52 to 1.58.

The glass flake preferably has an average particle diameter of 1 to 1000 μm, even 3 to 500 μm, and particularly 5 to 200 μm. The average particle diameter of the glass flake is determined as a particle diameter (D50) at 50% by volume in a cumulative undersize distribution of light scattering-based particle sizes measured by laser diffractometry.

To obtain a high-brightness reflected light of a neutral color, it is preferable that a product of the optical thickness of the glass flake and the optical thickness of the titanium oxide layer is set to be 61000 to 66000, even 61100 to 65800, particularly 61300 to 65700, and, in some cases, 61500 to 65500. The product of the optical thicknesses is described as a product of values expressed in nm. On the assumption that the product of the optical thicknesses is in the above range, the optical thickness of the glass flake is preferably 400 nm to 850 nm, more preferably 420 nm to 830 nm, and particularly preferably 430 nm to 820 nm, and may be 450 nm to 810 nm.

When the glitter pigment is to be dispersed in a thin paint film, the physical thickness of the glass flake is preferably 500 nm or less, more preferably 470 nm or less, and particularly preferably 450 nm or less, and may be 420 nm or less. Taking, for example, a production yield decreased by damage into consideration, the physical thickness of the glass flake is preferably 300 nm or more and particularly preferably 350 nm or more, and may be 370 nm or more.

There are production methods already established to form glass flakes having a desired thickness. Such glass flake production methods include a blow process and rotary process.

Figure 3:
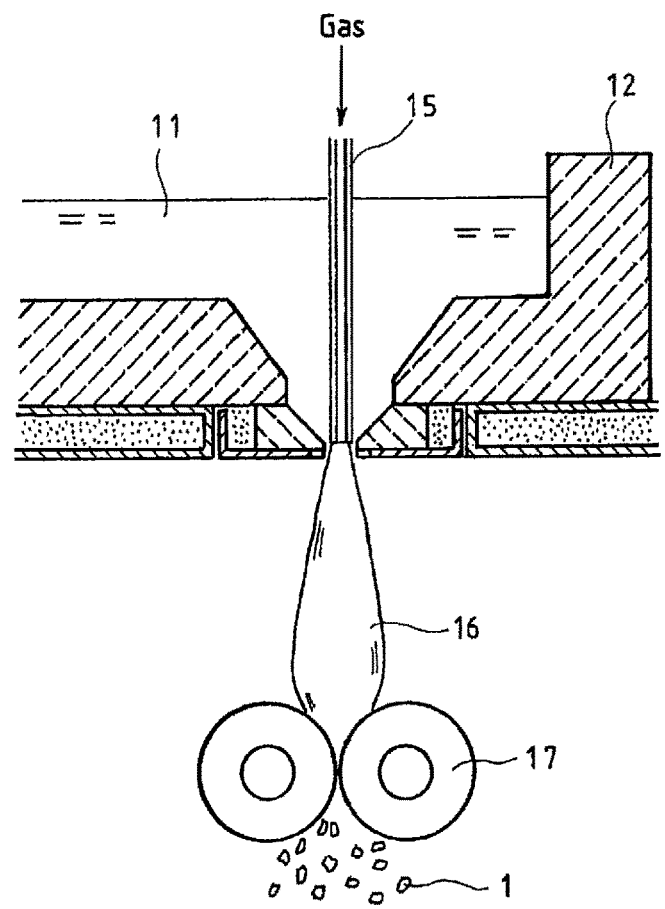
FIG. 3 is a schematic diagram illustrating an exemplary apparatus for producing glass flakes.

FIG. 3 shows an example of an apparatus for producing glass flakes by the blow process. The production apparatus is equipped with a refractory tank furnace 12, blowing nozzle 15, and pressing rolls 17. A glass raw material 11 is melted in the refractory tank furnace 12 (melting furnace) and is inflated into a balloon by a gas delivered through the blowing nozzle 15, so that hollow glass 16 is obtained. The hollow glass 16 is crushed by the pressing rolls 17 to obtain a glass flake 1. The thickness of the glass flake 1 can be controlled by adjusting, for example, the speed of pulling the hollow glass 16 and flow rate of the gas delivered through the blowing nozzle 15.

Figure 4:
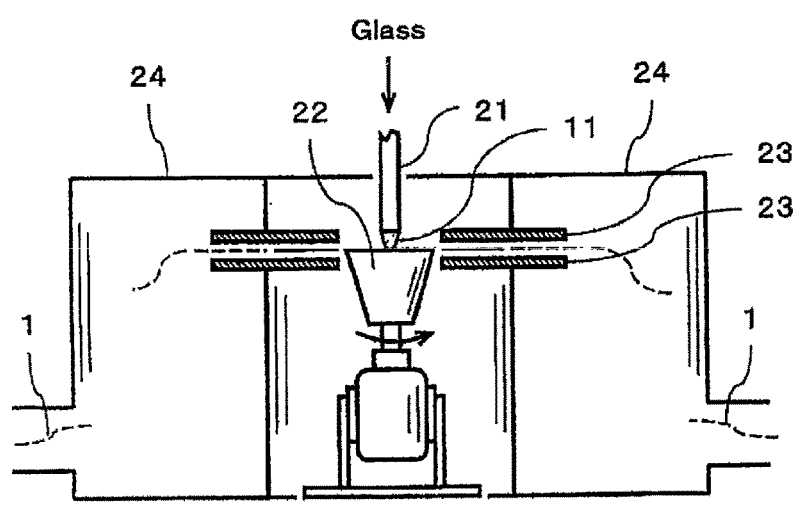
FIG. 4 is a schematic diagram illustrating another exemplary apparatus for producing glass flakes.

FIG. 4 shows an example of an apparatus for producing glass flakes by the rotary process. The apparatus is equipped with a rotary cup 22, pair of annular plates 23, and annular cyclone collector 24. A molten glass raw material 11 is poured into the rotary cup 22, centrifugally flows out from the upper edge of the rotary cup 22 in a radial manner, and is then drawn and carried into the annular cyclone collector 24 through the gap between the annular plates 23 by airflow. While passing through the annular plates 23, the glass is cooled and solidified into a thin film, which is then crushed into fine pieces to give a glass flake 1. The thickness of the glass flake 1 can be controlled by adjusting, for example, the distance between the annular plates 23 and velocity of the airflow.

[Titanium Oxide Layer]

There is a method already established to form a titanium oxide layer having a desired thickness and crystalline form on a flaky substrate such as a glass flake, and the method is well known. The titanium oxide layer is formed so that the product of the optical thickness thereof and the optical thickness of the glass flake will be in the above range. On that basis, the optical thickness of the titanium oxide layer is preferably 60 nm to 165 nm, more preferably 70 nm to 160 nm, and particularly preferably 75 nm to 150 nm, and may be 78 nm to 145 nm. The physical thickness of the titanium oxide layer is preferably 30 nm to 82 nm, more preferably 35 nm to 80 nm, and particularly preferably 37 nm to 75 nm, and may be 39 nm to 72 nm.

The titanium oxide layer is preferably composed of rutile-type titanium oxide. The anatase type is also known as a crystalline form of titanium oxide. However, anatase-type titanium oxide is highly active as a photocatalyst and may decompose a surrounding organic substance. For the titanium oxide layer for forming the optical interference unit, rutile-type titanium oxide having a high refractive index and being in a relatively stable crystalline form is suitable.

The rutile-type titanium oxide layer can be formed by heating anatase-type titanium oxide to a temperature as high as about 800° C. for transformation to rutile-type titanium oxide. Alternatively, the rutile-type titanium oxide layer can be formed, with no need for high-temperature heating, by attaching a tin compound to a surface where the titanium oxide layer is to be formed to deposit titanium oxide. The detail of the latter method is disclosed, for example, in Patent Literature 2 and JP 2001-031421 A.

[Silver Layer]

There are methods already established to form a silver layer having a desired thickness on a flaky substrate such as a glass flake, and the methods are well known. Sputtering and CVD, for example, are known as the methods for forming silver layers. However, for forming layers on glass flakes, electroless plating is suitable because a layer having a uniform thickness and covering the entire substrate is easily formed. Silver nitrate is commonly used as a material in electroless plating.

Too thick a silver layer makes it impossible to achieve good electromagnetic wave transmission properties. The physical thickness of the silver layer is suitably 55 nm or less, preferably 50 nm or less, and more preferably 47 nm or less, and may be 45 nm or less. The thickness of an aluminum flake is typically about 0.3 μm. Even a silver layer having a physical thickness of 60 nm has electromagnetic wave-shielding performance about half as high as the electromagnetic wave-shielding performance of an aluminum flake having a physical thickness of 0.2 μm. The electromagnetic wave-shielding performance of the silver layer having a physical thickness of 55 nm is sufficiently lower than half of the electromagnetic wave-shielding performance of an aluminum flake having a thickness around the typical thickness value.

Too thin a silver layer, on the other hand, makes it difficult to achieve good optical properties. Therefore, the physical thickness of the silver layer is suitably 35 nm or more, preferably 36 nm or more, and more preferably 37 nm or more, and may be 38 nm or more.

[Pigment-Containing Composition and Pigment-Containing Painted Product]

The glitter pigment according to the present invention exhibits a vivid whitish color when incorporated in various compositions. In another aspect, the present invention provides a pigment-containing composition containing the glitter pigment according to the present invention. An example of the pigment-containing composition is at least one selected from a paint, ink, cosmetic, and resin composition. Examples of the resin composition include those containing a resin which is PMMA and/or polycarbonate in addition to the glitter pigment. The resin composition may be a molded product of artificial marble.

In still another aspect, the present invention provides a pigment-containing painted product including: a substrate material; and a paint film formed on the substrate material, the paint film containing the glitter pigment according to the present invention. The pigment-containing painted product may be painted paper. In this case, the substrate material is paper. The substrate material is not limited to paper, and may be a metal, resin, ceramic, or another material. The paint film may be composed of the pigment-containing composition according to the present invention or may be formed by applying the pigment-containing composition according to the present invention onto the substrate material.

[Optical Simulation]

The relationship between the thicknesses of the glass and layers and the light transmission properties and light reflection properties was calculated for pigments each including a titanium oxide layer and silver layer formed in this order on a glass flake to form an optical interference system together with the glass flake. As is well known, the optical properties including the transmission properties and reflection properties can be calculated based on the straightness of light, law of reflection, and the law of refraction (Snell's law) from the refractive indices (n) and extinction coefficients (k), at a certain wavelength, of the materials of the laminate structure (flaky substrate and layers) and the thicknesses of the flaky substrate and layers. It is well known that the reflection properties calculated by means of the theory of geometrical optics well correspond to the properties of an actual product.

A model of the structure used for the calculation is the surrounding (external environment)/Ag/TiO$_2$/the glass flake/TiO$_2$/Ag/the surrounding (external environment). It was assumed that the glass flake was made of soda-lime glass and the titanium oxide layer was made of rutile-type titanium oxide. The external environment was assumed to be air (refractive index: 1.0). It was assumed that the light source was illuminant D65, the incident angle of light was 5°, and the location of measurement of reflected light was in a direction of a reflection angle of 5°. The following tables show the results for the calculation of the properties. T and R respectively refer to the visible light transmittance (%) and visible light reflectance (%) defined in Japanese Industrial Standards (JIS) R 3106:1998, and the values of L*, a*, and b* are based on the L*a*b* color system.

The transmission properties as well as the reflection properties were evaluated taking into consideration the fact that a portion of light passing through a glitter pigment is reflected by a backing material and be a portion of reflected light. When transmitted light is deeply colored, (that is, when absolute values of a* and/or b* are large,) reflected light of a sufficiently neutral color cannot be obtained.

TABLE 1

| | Physical thickness (nm) | | | Optical thickness (nd) | | | Product of optical thicknesses (A)*(B)/ 10000 | Optical transmission properties | | | | Optical reflection properties | | | |
|---|---|---|---|---|---|---|---|---|---|---|---|---|---|---|---|
| | Flake | TiO$_2$ | Ag | Flake (A) | TiO$_2$ (B) | Ag (C) | | T | L* | a* | b* | R | L* | a* | b* |
| Example | 288 | 70 | 40 | 438 | 140 | 5.4 | 6.13 | 4 | 22 | −26 | −1 | 90 | 96 | 7 | −1 |
| Example | 300 | 70 | 40 | 456 | 140 | 5.4 | 6.38 | 3 | 21 | −2 | −17 | 90 | 96 | 3 | 1 |
| Example | 308 | 70 | 40 | 468 | 140 | 5.4 | 6.55 | 5 | 26 | −15 | 9 | 90 | 96 | 3 | −2 |
| Comparative Example | 300 | 65 | 40 | 456 | 130 | 5.4 | 5.93 | 5 | 27 | −41 | 12 | 88 | 95 | 9 | −3 |
| Example | 300 | 68 | 40 | 456 | 136 | 5.4 | 6.20 | 4 | 22 | −23 | 5 | 92 | 97 | 3 | −1 |
| Example | 300 | 70 | 40 | 456 | 140 | 5.4 | 6.38 | 3 | 21 | −2 | −17 | 90 | 96 | 3 | 1 |
| Example | 300 | 72 | 40 | 456 | 144 | 5.4 | 6.57 | 3 | 22 | −3 | −10 | 93 | 97 | −1 | 3 |
| Comparative Example | 300 | 84 | 40 | 456 | 168 | 5.4 | 7.66 | 2 | 15 | 35 | −32 | 95 | 98 | −5 | 5 |
| Example | 300 | 70 | 36 | 456 | 140 | 4.9 | 6.38 | 5 | 26 | −2 | −18 | 90 | 96 | 2 | 3 |
| Example | 300 | 70 | 50 | 456 | 140 | 6.8 | 6.38 | 2 | 14 | −14 | −1 | 91 | 96 | 5 | −3 |

TABLE 2

| | Physical thickness (nm) | | | Optical thickness (nd) | | | Product of optical thicknesses (A)*(B)/ 10000 | Optical transmission properties | | | | Optical reflection properties | | | |
|---|---|---|---|---|---|---|---|---|---|---|---|---|---|---|---|
| | Flake | TiO$_2$ | Ag | Flake (A) | TiO$_2$ (B) | Ag (C) | | T | L* | a* | b* | R | L* | a* | b* |
| Comparative Example | 330 | 54 | 40 | 502 | 108 | 5.4 | 5.42 | 4 | 23 | −35 | 6 | 92 | 97 | 5 | −1 |
| Example | 380 | 54 | 40 | 578 | 108 | 5.4 | 6.24 | 4 | 25 | 15 | −5 | 91 | 96 | −4 | 1 |
| Example | 395 | 54 | 40 | 600 | 108 | 5.4 | 6.48 | 2 | 17 | 24 | −17 | 93 | 97 | −6 | 2 |
| Example | 399 | 54 | 40 | 606 | 108 | 5.4 | 6.55 | 2 | 16 | 28 | −27 | 95 | 98 | −4 | 4 |
| Comparative Example | 480 | 54 | 40 | 730 | 108 | 5.4 | 7.88 | 4 | 24 | −31 | −14 | 91 | 96 | 6 | 4 |
| Comparative Example | 400 | 50 | 40 | 608 | 100 | 5.4 | 6.08 | 3 | 18 | 34 | −36 | 94 | 98 | −7 | 10 |
| Example | 400 | 51 | 40 | 608 | 102 | 5.4 | 6.20 | 4 | 23 | 28 | −16 | 93 | 97 | −7 | 5 |
| Example | 400 | 53 | 40 | 608 | 106 | 5.4 | 6.44 | 2 | 15 | 25 | −23 | 95 | 98 | −4 | 3 |
| Example | 400 | 54 | 40 | 608 | 108 | 5.4 | 6.57 | 2 | 18 | 30 | −28 | 94 | 98 | −5 | 5 |
| Comparative Example | 400 | 95 | 40 | 608 | 190 | 5.4 | 11.55 | 4 | 22 | −36 | 9 | 93 | 97 | 4 | 0 |
| Example | 400 | 53 | 45 | 608 | 106 | 6.1 | 6.44 | 1 | 9 | 23 | −25 | 96 | 99 | −3 | 3 |
| Example | 400 | 53 | 50 | 608 | 106 | 6.8 | 6.44 | 0 | 4 | 14 | −19 | 97 | 99 | −1 | 2 |

TABLE 3

| | Physical thickness (nm) | | | Optical thickness (nd) | | | Product of optical thicknesses (A)*(B)/ 10000 | Optical transmission properties | | | | Optical reflection properties | | | |
|---|---|---|---|---|---|---|---|---|---|---|---|---|---|---|---|
| | Flake | TiO$_2$ | Ag | Flake (A) | TiO$_2$ (B) | Ag (C) | | T | L* | a* | b* | R | L* | a* | b* |
| Comparative Example | 430 | 40 | 40 | 654 | 80 | 5.4 | 5.23 | 2 | 18 | 36 | −40 | 94 | 98 | −7 | 1 |
| Example | 515 | 40 | 40 | 783 | 80 | 5.4 | 6.26 | 2 | 14 | −3 | −25 | 95 | 98 | 2 | 3 |
| Example | 520 | 40 | 40 | 790 | 80 | 5.4 | 6.32 | 3 | 18 | −3 | −28 | 94 | 98 | 1 | −7 |
| Example | 530 | 40 | 40 | 806 | 80 | 5.4 | 6.44 | 2 | 16 | −16 | −15 | 94 | 98 | 4 | 2 |
| Example | 535 | 40 | 40 | 813 | 80 | 5.4 | 6.51 | 3 | 19 | −12 | −21 | 94 | 98 | 2 | 3 |
| Comparative Example | 560 | 40 | 40 | 851 | 80 | 5.4 | 6.81 | 2 | 18 | 17 | −41 | 93 | 97 | 0 | 8 |
| Comparative Example | 500 | 25 | 40 | 760 | 50 | 5.4 | 3.80 | 2 | 13 | 32 | −27 | 94 | 98 | −7 | 5 |
| Example | 500 | 41 | 40 | 760 | 82 | 5.4 | 6.23 | 2 | 14 | −10 | −14 | 95 | 98 | 0 | 2 |
| Example | 500 | 42 | 40 | 760 | 84 | 5.4 | 6.38 | 2 | 14 | 1 | −26 | 95 | 98 | −6 | 4 |
| Example | 500 | 43 | 40 | 760 | 86 | 5.4 | 6.54 | 2 | 16 | −13 | −14 | 94 | 97 | 4 | 1 |
| Comparative Example | 500 | 42 | 30 | 760 | 84 | 4.1 | 6.38 | 7 | 26 | −27 | −14 | 88 | 95 | 8 | 3 |
| Example | 500 | 42 | 45 | 760 | 84 | 6.1 | 6.38 | 1 | 11 | −25 | −6 | 96 | 98 | 2 | 1 |
| Example | 500 | 42 | 50 | 760 | 84 | 6.8 | 6.38 | 5 | 5 | −8 | −7 | 97 | 99 | 1 | 1 |

As shown in Tables 1 to 3, when a product of the optical thickness (A) of the glass flake and the optical thickness (B) of the titanium oxide layer is $6.1 \times 10^4$ to $6.6 \times 10^4$ and the physical thickness of the silver layer is 35 nm to 55 nm, the color of transmitted light as well as that of reflected light is neutral and the reflectance R is 90% or more.

The invention claimed is:

1. A glitter pigment, comprising:
    a glass flake;
    a titanium oxide layer and a silver layer formed in this order on the glass flake,
    wherein a product of the optical thickness of the glass flake and the optical thickness of the titanium oxide layer is 61000 or more and 66000 or less when the optical thickness is expressed in nm,
    the optical thickness of the titanium oxide layer is 60 nm or more and 165 nm or less, and
    the silver layer has a physical thickness of 35 nm or more and 55 nm or less.

2. The glitter pigment according to claim 1, wherein the product is 61300 or more and 65700 or less.

3. The glitter pigment according to claim 1, wherein the glass flake has a physical thickness of 300 nm or more and 500 nm or less.

4. The glitter pigment according to claim 1, wherein the titanium oxide layer has a physical thickness of 35 nm or more and 80 nm or less.

5. A pigment-containing composition, comprising the glitter pigment according to claim 1.

6. A pigment-containing painted product, comprising:
    a substrate material; and
    a paint film formed on the substrate material, the paint film containing the glitter pigment according to claim 1.

7. The glitter pigment according to claim 1, wherein the glitter pigment exhibits a color in appearance in which, as measured by L*, a*, and b* based on the L*a*b* color system, the absolute values of a* and/or b* are 30 or less.

8. The glitter pigment according to claim 1, wherein the optical thickness of the glass flake is 400 nm or more and 850 nm or less.

* * * * *